(12) United States Patent
Patnala et al.

(10) Patent No.: US 12,023,506 B2
(45) Date of Patent: Jul. 2, 2024

(54) DIAGNOSTIC SYSTEMS AND METHODS FOR USE DURING A PROCEDURE ASSOCIATED WITH A COCHLEAR IMPLANT

(71) Applicant: Advanced Bionics AG, Staefa (CH)

(72) Inventors: Anil K. Patnala, Stevenson Ranch, CA (US); Mark Londborg, West Hills, CA (US); Kanthaiah Koka, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 276 days.

(21) Appl. No.: 17/417,337

(22) PCT Filed: Dec. 28, 2018

(86) PCT No.: PCT/US2018/067900
§ 371 (c)(1),
(2) Date: Jun. 22, 2021

(87) PCT Pub. No.: WO2020/139375
PCT Pub. Date: Jul. 2, 2020

(65) Prior Publication Data
US 2022/0072319 A1    Mar. 10, 2022

(51) Int. Cl.
*A61N 1/36*   (2006.01)
*A61N 1/05*   (2006.01)
*A61N 1/372*  (2006.01)

(52) U.S. Cl.
CPC ....... *A61N 1/37241* (2013.01); *A61N 1/0541* (2013.01); *A61N 1/36038* (2017.08); *A61N 1/37247* (2013.01); *A61N 1/37282* (2013.01)

(58) Field of Classification Search
CPC ............ A61N 1/36036; A61N 1/36038; A61N 1/36039
See application file for complete search history.

(56) References Cited

U.S. PATENT DOCUMENTS

| 7,137,946 B2 | 11/2006 | Waldmann |
| 7,616,999 B2 | 11/2009 | Overstreet et al. |

(Continued)

FOREIGN PATENT DOCUMENTS

| WO | 2013008057 | 1/2013 |
| WO | 2017065809 | 4/2017 |
| WO | 2018171885 | 9/2018 |

OTHER PUBLICATIONS

International Search Report and Written Opinion received in International Application No. PCT/US18/67900.

*Primary Examiner* — George R Evanisko
(74) *Attorney, Agent, or Firm* — ALG Intellectual Property, LLC

(57) ABSTRACT

A diagnostic system for use during a procedure associated with a cochlear implant includes a computing module and a base module configured to attach to a back side of the computing module and serve as a stand for the computing module. The computing module includes a display screen and a processor configured to execute a diagnostic application and direct the display screen to display a graphical user interface associated with the diagnostic application. The base module includes an interface unit configured to be communicatively coupled to the processor and to the cochlear implant while the base module is attached to the back side of the computing module.

18 Claims, 15 Drawing Sheets

(56) References Cited

U.S. PATENT DOCUMENTS

| | | | |
|---|---|---|---|
| 7,657,319 B2 | 2/2010 | Goetz et al. | |
| 7,974,702 B1 * | 7/2011 | Fain | A61N 1/37211 |
| | | | 607/32 |
| 8,532,775 B2 * | 9/2013 | Berg | A61B 5/0028 |
| | | | 607/30 |
| 8,542,842 B2 | 9/2013 | Zaccaria | |
| 9,020,601 B2 | 4/2015 | Meskens et al. | |
| 9,101,306 B2 * | 8/2015 | Bernini | A61B 5/0024 |
| 9,155,887 B2 | 10/2015 | Miller, III et al. | |
| 9,272,142 B2 | 3/2016 | Botros et al. | |
| 9,533,162 B2 | 1/2017 | Ter-Petrosyan et al. | |
| 9,550,061 B2 | 1/2017 | Litvak et al. | |
| 9,707,402 B2 | 7/2017 | Aghassian | |
| 9,883,299 B2 | 1/2018 | Howes | |
| 10,004,909 B2 | 6/2018 | Tahmasian | |
| 10,029,097 B2 | 7/2018 | McLaughlin | |
| 2006/0287690 A1 | 12/2006 | Bouchataoui et al. | |
| 2011/0060384 A1 | 3/2011 | Lineaweaver | |
| 2011/0313315 A1 | 12/2011 | Attias et al. | |
| 2013/0339039 A1 | 12/2013 | Roman et al. | |
| 2014/0067015 A1 | 3/2014 | Kothandaraman et al. | |
| 2015/0237452 A1 | 8/2015 | Vanpoucke | |
| 2017/0001008 A1 * | 1/2017 | Hunt | A61N 1/37258 |
| 2017/0287504 A1 | 10/2017 | Vogel et al. | |
| 2018/0050197 A1 | 2/2018 | Mazanec et al. | |
| 2018/0110982 A1 | 4/2018 | Heasman et al. | |
| 2018/0154150 A1 | 6/2018 | Boven et al. | |
| 2018/0229035 A1 | 8/2018 | Koka et al. | |
| 2018/0275956 A1 | 9/2018 | Reed et al. | |
| 2018/0288541 A1 | 10/2018 | Chalupper et al. | |
| 2018/0304069 A1 * | 10/2018 | Koka | A61N 1/36039 |

\* cited by examiner

DIAGNOSTIC SYSTEMS AND METHODS FOR USE DURING A PROCEDURE ASSOCIATED WITH A COCHLEAR IMPLANT

BACKGROUND INFORMATION

During and after a surgical procedure in which a cochlear implant and an electrode lead are implanted within a recipient, it may be desirable to perform various diagnostic operations associated with the cochlear implant, electrode lead, and/or recipient. For example, during an insertion procedure in which an electrode lead is placed within the cochlea, it may be desirable to monitor evoked responses (e.g., electrocochleographic ("ECoG" or "ECochG") potentials) that occur within the recipient in response to acoustic stimulation applied to the recipient. These evoked responses may be indicative of electrode positioning within the cochlea, trauma that may occur to the cochlea during the insertion procedure, residual hearing of different areas of the cochlea as the electrode lead is inserted, and/or various other factors associated with the insertion procedure.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
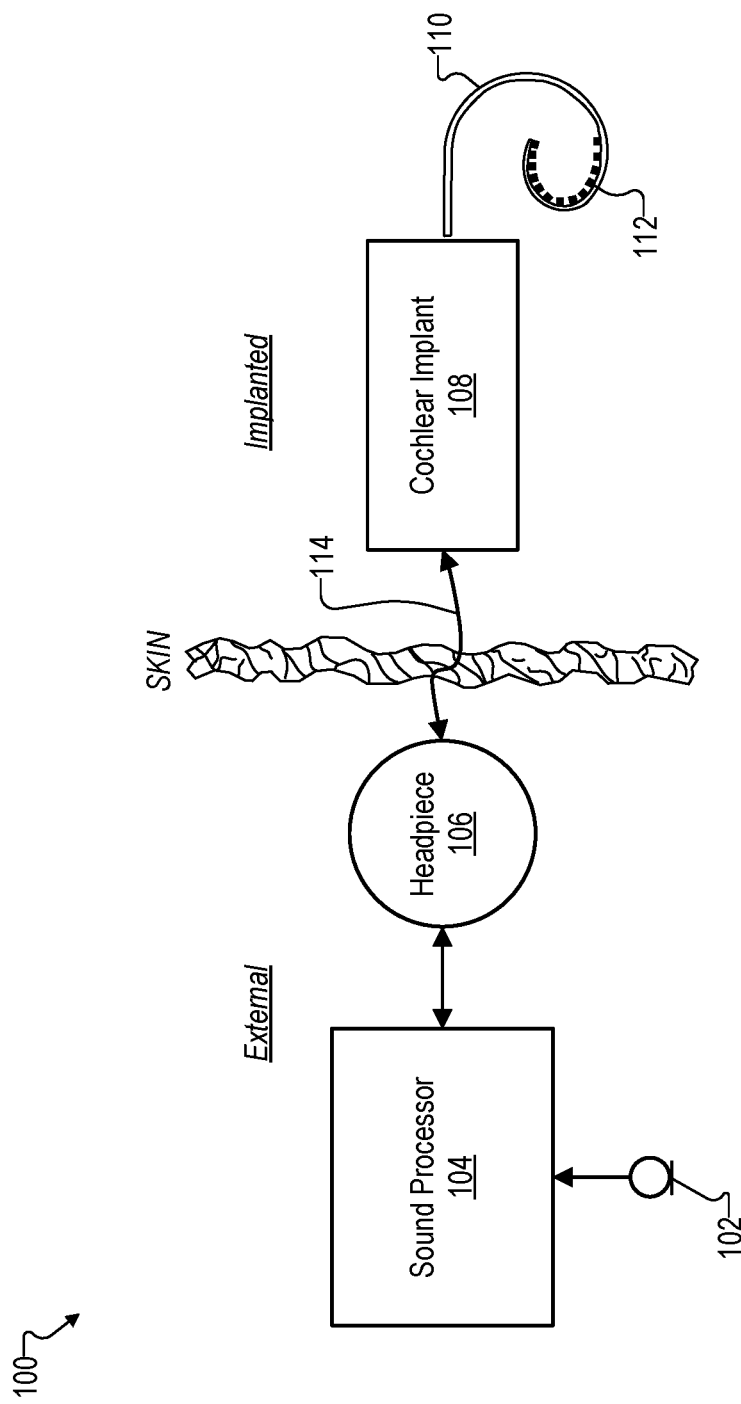
FIG. 1 illustrates an exemplary cochlear implant system according to principles described herein.

Diagnostic systems and methods for use during a procedure associated with a cochlear implant are described herein. As will be described in more detail below, an exemplary diagnostic system includes a computing module and a base module. The base module is configured to attach to the computing module and serve as a stand for the computing module. The computing module includes a display screen and a processor configured to execute a diagnostic application and direct the display screen to display a graphical user interface associated with the diagnostic application. The base module houses an interface unit configured to be communicatively coupled to the processor and to the cochlear implant while the base module is attached to the computing module.

In some examples, the base module includes an audio output port configured to be selectively coupled to a sound delivery apparatus (e.g., tubing having an ear insert configured to be positioned within or near an entrance to an ear canal of a recipient of the cochlear implant) and a communications port configured to be selectively coupled to a coil configured to wirelessly communicate with the cochlear implant. In this configuration, the interface unit may generate acoustic stimulation and deliver the acoustic stimulation to the recipient by way of the audio output port and the sound delivery apparatus. The interface unit may receive recording data associated with the acoustic stimulation from the cochlear implant by way of the coil and the communications port.

In some examples, the recording data is representative of an evoked response that occurs within the recipient in response to the acoustic stimulation. The evoked response may be an ECoG potential (e.g., a cochlear microphonic potential, an action potential, a summating potential, etc.), an auditory nerve response, a brainstem response, a compound action potential, a stapedius reflex, and/or any other type of neural or physiological response that may occur within a recipient in response to application of acoustic stimulation to the recipient. Evoked responses may originate from neural tissues, hair cell to neural synapses, inner or outer hair cells, or other sources. The evoked responses may additionally or alternatively occur in response to electrical stimulation.

The recording data received by the interface unit may be transmitted by the interface unit to the processor of the computing module. The processor may process the recording data in accordance with the diagnostic application. Examples of this are provided in more detail below.

The diagnostic systems and methods described herein provide a hardware platform that may be used in an operating room to perform various diagnostic operations during a procedure associated with a cochlear implant. Exemplary diagnostic operations and procedures that may be performed in accordance with the systems and methods described herein are described in more detail in co-pending PCT Application No. PCT/US2018/068054, co-pending PCT Application No. PCT/US2018/068055, co-pending U.S. application Ser. No. 16/236,300, and co-pending U.S. application Ser. No. 16/236,303, each of which is filed the same day as the present application and incorporated herein by reference in its entirety.

As one example, the diagnostic systems and methods described herein may be used to monitor evoked responses that occur in response to acoustic stimulation applied during an insertion procedure in which an electrode lead connected to a cochlear implant is inserted into a cochlea of a recipient. The processor of the computing module may direct the display screen to display one or more graphical user interfaces associated with the evoked responses. In this manner, a surgeon (or other user) may receive real-time monitoring feedback that assists the surgeon in correctly positioning the electrode lead.

The systems and methods described herein may also be used in environments outside the operating room. For example, the base module may be detached from the computing module and communicatively coupled to a computing device located, for example, in a clinician's office. The computing device may utilize the base module to perform various diagnostic procedures with respect to a recipient who has already been implanted with a cochlear implant. For example, the computing device may direct the interface unit included in the base module to apply acoustic stimulation to a cochlear implant recipient and receive recording data representative of evoked responses that occur within the recipient in response to the acoustic stimulation. This data may be used by the computing device to adjust one or more parameters associated with the cochlear implant. In this manner, an entity (e.g., a surgical center that performs surgery and that performs various postoperative procedures) may only need to purchase a single diagnostic system in order to have diagnostic functionality within and outside the operating room.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into a cochlea of a recipient to stimulate the cochlea when the distal portion of electrode lead 110 is inserted into the cochlea. One or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. As shown, electrode lead 110 may be pre-curved so as to properly fit within the spiral shape of the cochlea. Additional or alternative components may be included within cochlear implant system 100 as may serve a particular implementation.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a clinician's programming interface (CPI) device, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bidirectional communication link and/or one or more dedicated unidirectional communication links as may serve a particular implementation).

Cochlear implant 108 may include any suitable type of implantable stimulator. For example, cochlear implant 108 may be implemented by an implantable cochlear stimulator. Additionally or alternatively, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
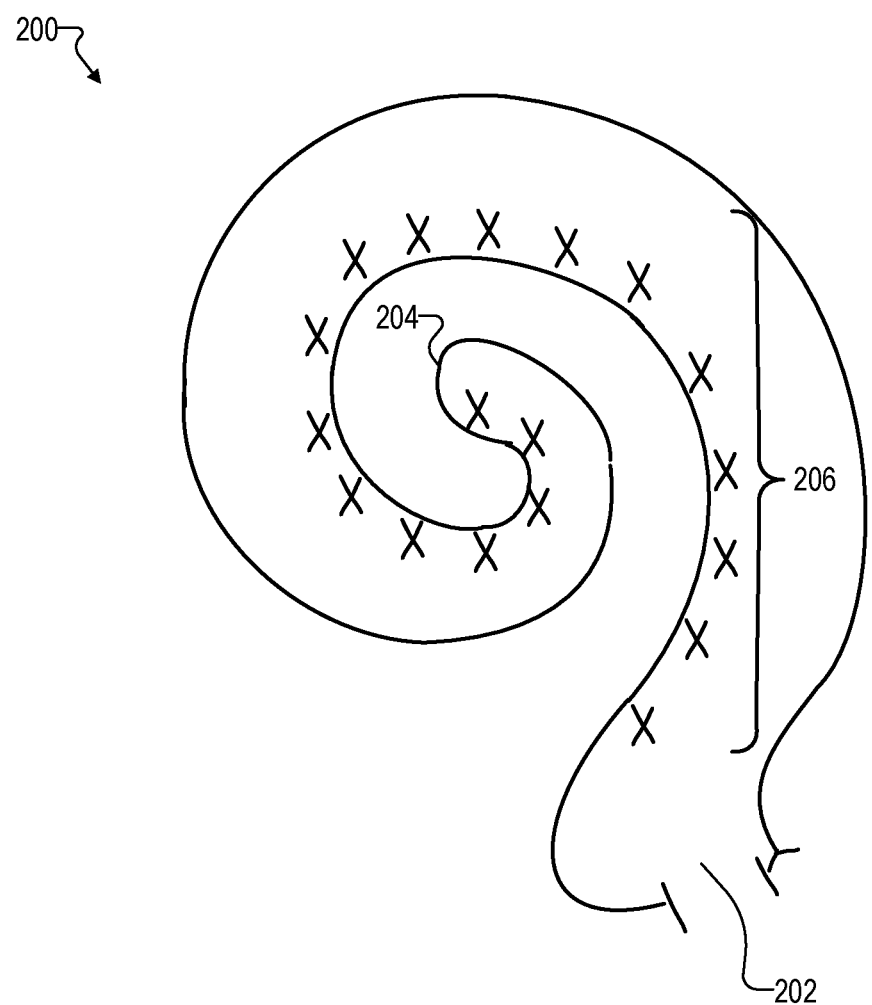
FIG. 2 illustrates a schematic structure of the human cochlea according to principles described herein.

FIG. 2 illustrates a schematic structure of the human cochlea 200 into which electrode lead 110 may be inserted.

As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

The diagnostic systems and methods described herein may be used during a procedure associated with a cochlear implant, such as cochlear implant 108. For example, the diagnostic systems and methods described herein may be used intraoperatively in an operating room during a surgical procedure associated with cochlear implant 108. To illustrate, the diagnostic systems and methods described herein may be used during a surgical procedure in which cochlear implant 108 and electrode lead 110 are implanted within a recipient and/or during a surgical procedure in which cochlear implant 108 and/or electrode lead 110 are explanted from a recipient. The diagnostic systems and methods described herein may additionally or alternatively be used postoperatively. For example, the diagnostic systems and methods described herein may be used to monitor cochlear health and/or performance by cochlear implant 108 immediately after cochlear implant 108 and/or electrode lead 110 have been implanted within a recipient. As another example, the diagnostic systems and methods described herein may be used in a clinician's office to adjust one or more operating parameters associated with a cochlear implant system already fitted to a recipient.

Figure 3:
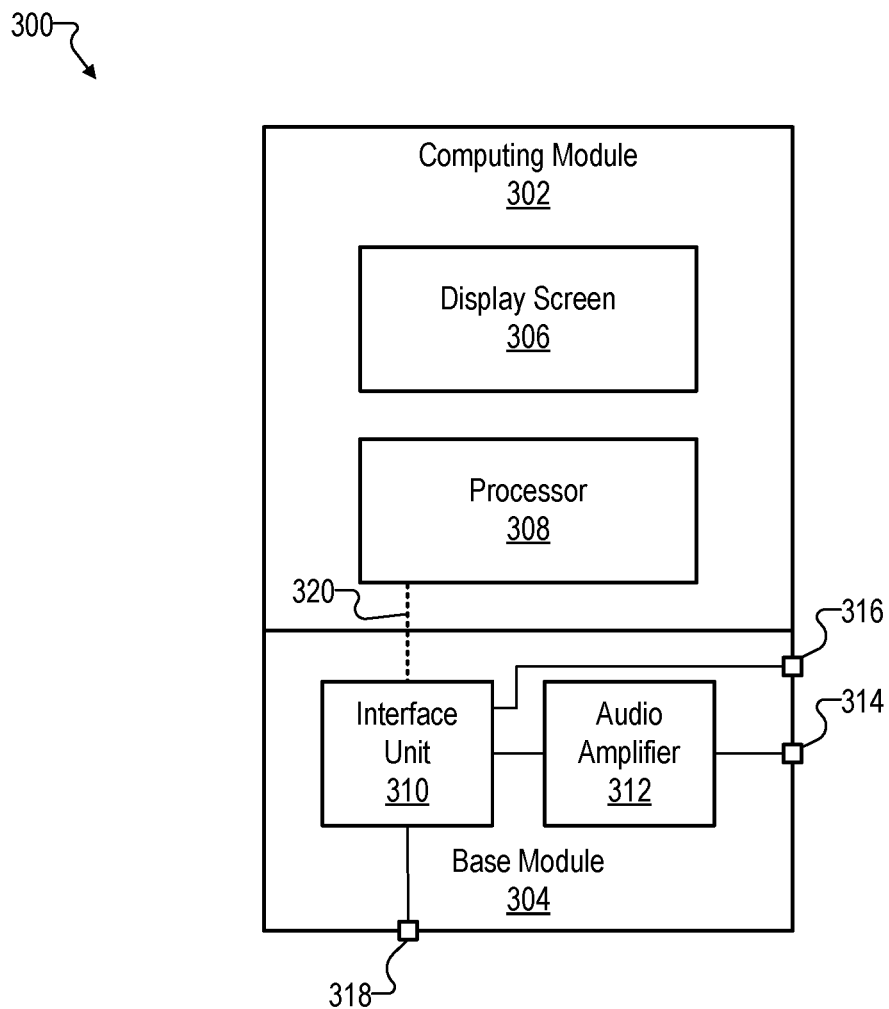
FIG. 3 illustrates an exemplary diagnostic system according to principles described herein.

FIG. 3 illustrates an exemplary diagnostic system 300. As shown, diagnostic system 300 includes a computing module 302 and a base module 304. Computing module 302 includes a display screen 306 and a processor 308. Base module 304 includes an interface unit 310, an audio amplifier 312, an audio output port 314, a communications port 316, and a port 318. Computing module 302 and base module 304 may include additional or alternative components, as will be described herein. Exemplary implementations of computing module 302 and base module 304 are described herein.

In the configuration shown in FIG. 3, base module 304 is physically attached to computing module 302. In this configuration, processor 302 is communicatively coupled to interface unit 310 by way of a connection 320. Connection 320 may be implemented by any suitable connection (e.g., an internal USB connection) as may serve a particular implementation. As will be described in more detail below, base module 304 may be selectively detached from computing module 302 and connected to a different computing device by way of port 318.

Display screen 306 may be configured to display any suitable content associated with an application executed by processor 308. Display screen 306 may be implemented by a touchscreen and/or any other type of display screen is may serve a particular implementation.

Processor 308 may be configured to execute a diagnostic application associated with a cochlear implant (e.g., cochlear implant 108). For example, processor 308 may execute a diagnostic application that may be used during a surgical procedure associated with the cochlear implant. The diagnostic application may be configured to perform various diagnostic operations associated with the cochlear implant during the surgical procedure. Exemplary diagnostic operations are described herein.

In some examples, processor 308 may direct display screen 306 to display a graphical user interface associated with the diagnostic application being executed by processor 308. A user may interact with the graphical user interface to adjust one or more parameters associated with the cochlear implant and/or otherwise obtain information that may be useful during a procedure associated with the cochlear implant.

Base module 304 may be configured to attach to computing module 302 and serve as a stand for computing module 302. Examples of these features are described herein.

Interface unit 310 is configured to be communicatively coupled to processor 308 by way of connection 320 while base module 304 is attached to computing module 302. Interface unit 310 is further configured to be communicatively coupled to the cochlear implant while base module 304 is attached to computing module 302. In this manner, interface unit 310 provides an interface between processor 308 and the cochlear implant.

Interface unit 310 may be communicatively coupled to the cochlear implant by way of communications port 316. For example, communications port 316 may be selectively coupled to a coil (e.g., a coil included in a headpiece, such as headpiece 106, or a disposable stand-alone coil, such as will be described herein) configured to wirelessly communicate with the cochlear implant. Interface unit 310 may communicate with the cochlear implant by transmitting and/or receiving data to/from the cochlear implant by way of the coil connected to communications port 316.

Interface unit 310 may be further configured to generate and provide acoustic stimulation (e.g., sound waves) to the recipient of the cochlear implant. To this end, audio output port 314 is configured to be selectively coupled to a sound delivery apparatus. As will be described below, the sound delivery apparatus may be implemented by tubing that has a distal portion configured to be placed in or near an entrance to an ear canal of a recipient of the cochlear implant. While the sound delivery apparatus is connected to audio output port 314, interface unit 310 may transmit the acoustic stimulation to the recipient by way of the sound delivery apparatus. Exemplary sound delivery apparatuses are described herein.

As shown, audio amplifier 312 may be positioned within a path between interface unit 310 and audio output port 314. In this configuration, audio amplifier 312 may be configured to amplify the acoustic stimulation before the acoustic stimulation is delivered to the recipient by way of audio output port 314 and the sound delivery apparatus. In some alternative examples, amplification of the acoustic stimulation generated by interface unit 310 is not necessary, thereby obviating the need for audio amplifier 312 to be included in base module 304. Hence, in some implementations, base module 304 does not include audio amplifier 312.

In some examples, diagnostic system 300 may be configured to self-calibrate and/or perform in-situ testing. For example, processor 308 may calibrate an amplitude level of acoustic stimulation generated by interface unit 310 before and/or during a surgical procedure. Such self-calibration and in-situ testing may be performed in any suitable manner.

Figure 4:
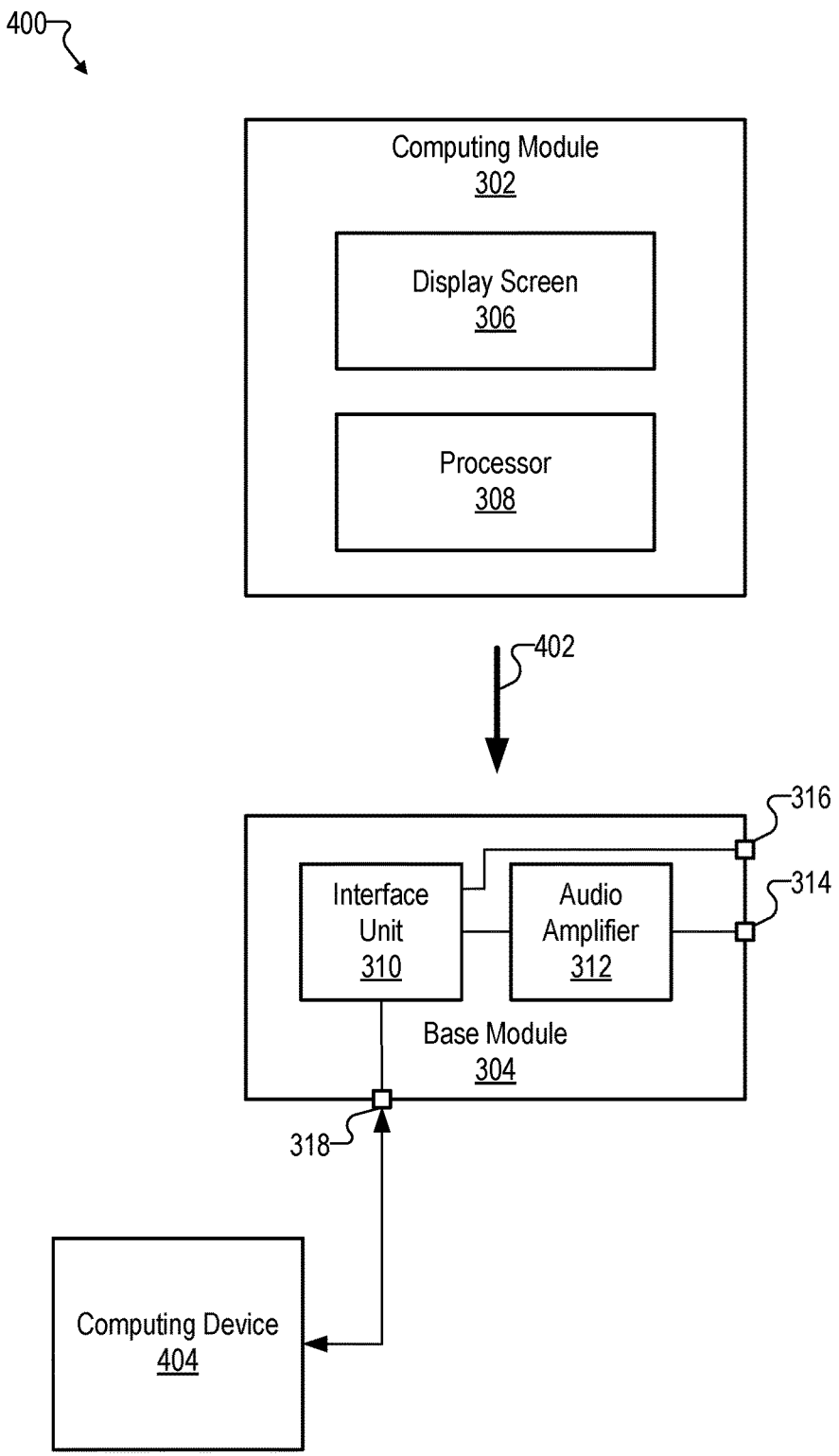
FIG. 4 shows a base module detached from a computing module according to principles described herein.

As mentioned, base module 304 may be selectively detached from computing module 302. To illustrate, FIG. 4 shows a configuration 400 in which base module 304 is detached from computing module 302. This detachment is illustrated by arrow 402. While detached, interface unit 310 of base module 304 may be communicatively coupled to a computing device 404. For example, interface unit 310 may be communicatively coupled to computing device 404 by plugging a cable (e.g., a USB cable) into port 318 and into computing device 404. In this configuration, computing device 404 may use interface unit 310 to interface with a cochlear implant (e.g., by providing acoustic stimulation to a recipient of the cochlear implant and/or receiving recording data from the cochlear implant).

Figure 5:
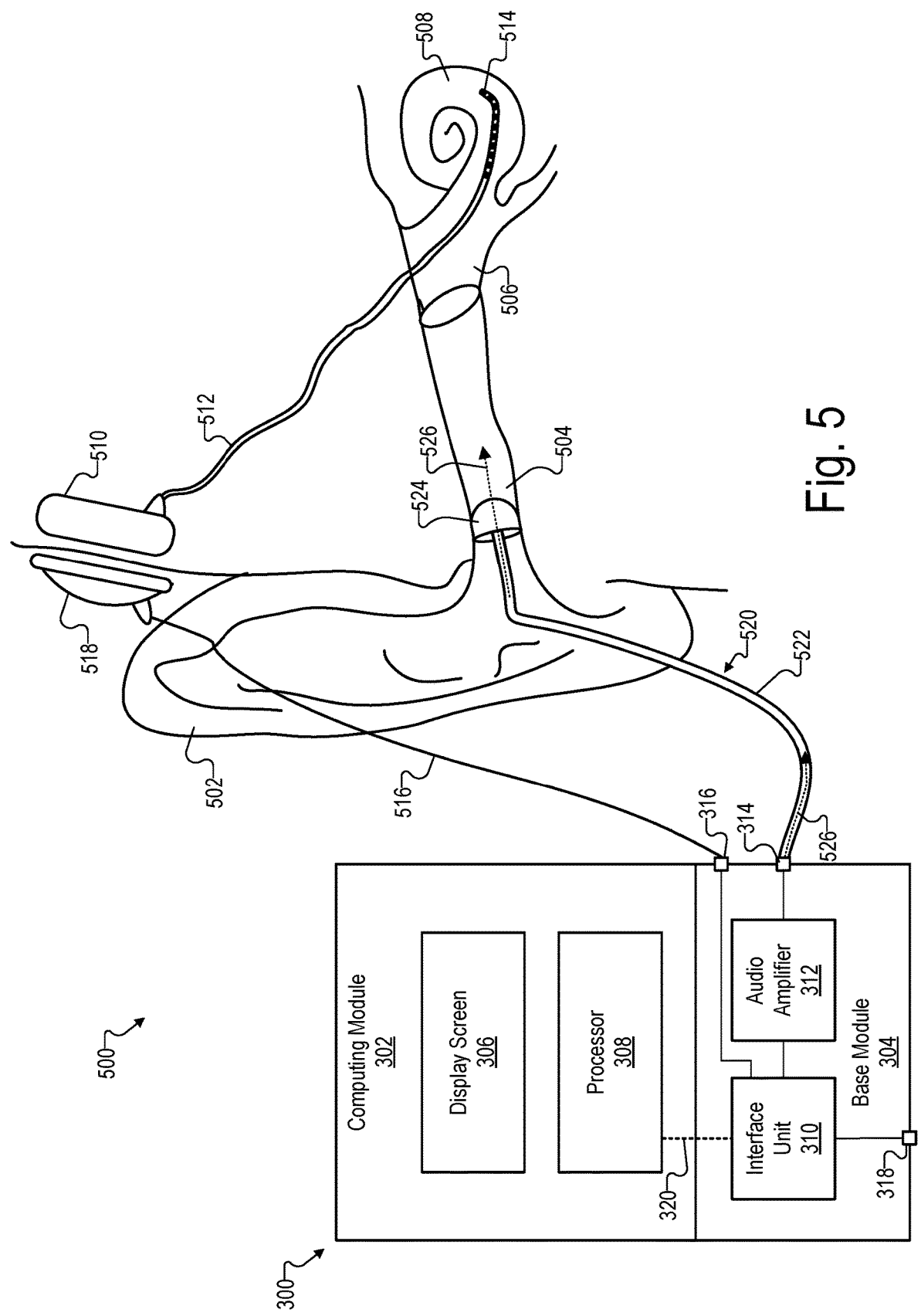
FIGS. 5-8 depict exemplary configurations in which a diagnostic system is used to perform one or more diagnostic operations during a surgical procedure involving a cochlear implant and an electrode lead according to principles described herein.

FIG. 5 depicts an exemplary configuration 500 in which diagnostic system 300 is used to perform one or more diagnostic operations during a surgical procedure involving a cochlear implant and an electrode lead. The surgical procedure may include, for example, an insertion procedure in which the cochlear implant is inserted into an incision pocket formed within the recipient and/or in which a distal portion of the electrode lead is positioned within the cochlea.

Various anatomical features of the recipient's ear are shown in FIG. 5. Specifically, anatomical features include a pinna 502 (i.e., the outer ear), an ear canal 504, a middle ear 506, and a cochlea 508. While no specific incision or other explicit surgical representation is shown in FIG. 5, it will be understood that such elements may be present when a surgical procedure is ongoing. For example, an incision may be present to allow the surgeon internal access to the recipient to insert the lead into cochlea 508. In some procedures, pinna 502 may be taped down and covered with surgical drapes so as to cover ear canal 504 (e.g., to help prevent fluids associated with the operation from reaching ear canal 504).

In the example of FIG. 5, a cochlear implant 510 and an electrode lead 512 are shown to be implanted within the recipient. Cochlear implant 510 may be similar, for example, to cochlear implant 108, and electrode lead 512 may be similar, for example, to electrode lead 110. Electrode lead 512 includes a plurality of electrodes (e.g., electrode 514, which is the distal-most electrode disposed on electrode lead 512).

As shown, a cable 516 of a headpiece 518 is connected to communications port 316. In this configuration, interface unit 310 may wirelessly communicate with cochlear implant 510 by way of a coil and/or other electronics included in headpiece 518, which may be similar to headpiece 106.

As also shown, a sound delivery apparatus 520 is connected to audio output port 314. Sound delivery apparatus 520 includes tubing 522 and an ear insert 524. Ear insert 524 is configured to fit at or within an entrance of ear canal 504. Tubing 522 and ear insert 524 together form a sound propagation channel 526 that delivers acoustic stimulation provided by interface unit 310 to the ear canal 504. Tubing 522 and ear insert 524 may be made out of any suitable material as may serve a particular implementation.

In some examples, processor 308 may execute a diagnostic application during the surgical procedure. In accordance with the diagnostic application, processor 308 may transmit, by way of connection 320, a command (also referred to as a stimulation command) to interface unit 310 for interface unit 310 to apply acoustic stimulation to the recipient and receive recording data representative of an evoked response that occurs within the recipient in response to the acoustic stimulation. In response to receiving the command, interface unit 310 may generate and apply the acoustic stimulation to the recipient by way of audio output port 314 and sound delivery apparatus 520. Interface unit 310 may also transmit a command (also referred to as a recording command) to cochlear implant 510 by way of communications port 316 and headpiece 518 for cochlear implant 510 to use electrode 514 to record the evoked response that occurs in response to the acoustic stimulation. Cochlear implant 510 may transmit the recording data back to interface unit 310 by way of headpiece 518 and communications port 316. Interface unit 310 may transmit the recording data to processor 308 by way of connection 320. Processor 308 may process the recording data and direct display screen 306 to display one or more graphical user interfaces associated with the recording data.

As another example, in accordance with the diagnostic application, processor 308 may transmit, by way of connection 320, a command to interface unit 310 for interface unit 310 to direct cochlear implant 510 to apply electrical stimulation to the recipient by way of one or more electrodes included on electrode lead 512. The command may further direct interface unit 310 to receive recording data representative of an evoked response that occurs within the recipient in response to the electrical stimulation. In response to receiving the command, interface unit 310 may transmit a command to cochlear implant 510 for cochlear implant 510 to generate and apply the electrical stimulation to the recipient by way of the one or more electrodes and for cochlear implant 510 to use one or more of electrodes included on electrode lead 512 to record the evoked response that occurs in response to the electrical stimulation. Cochlear implant 510 may transmit the recording data back to interface unit 310 by way of headpiece 518 and communications port 316. Interface unit 310 may transmit the recording data to processor 308 by way of connection 320. Processor 308 may process the recording data and direct display screen 306 to display one or more graphical user interfaces associated with the recording data.

Figure 6:
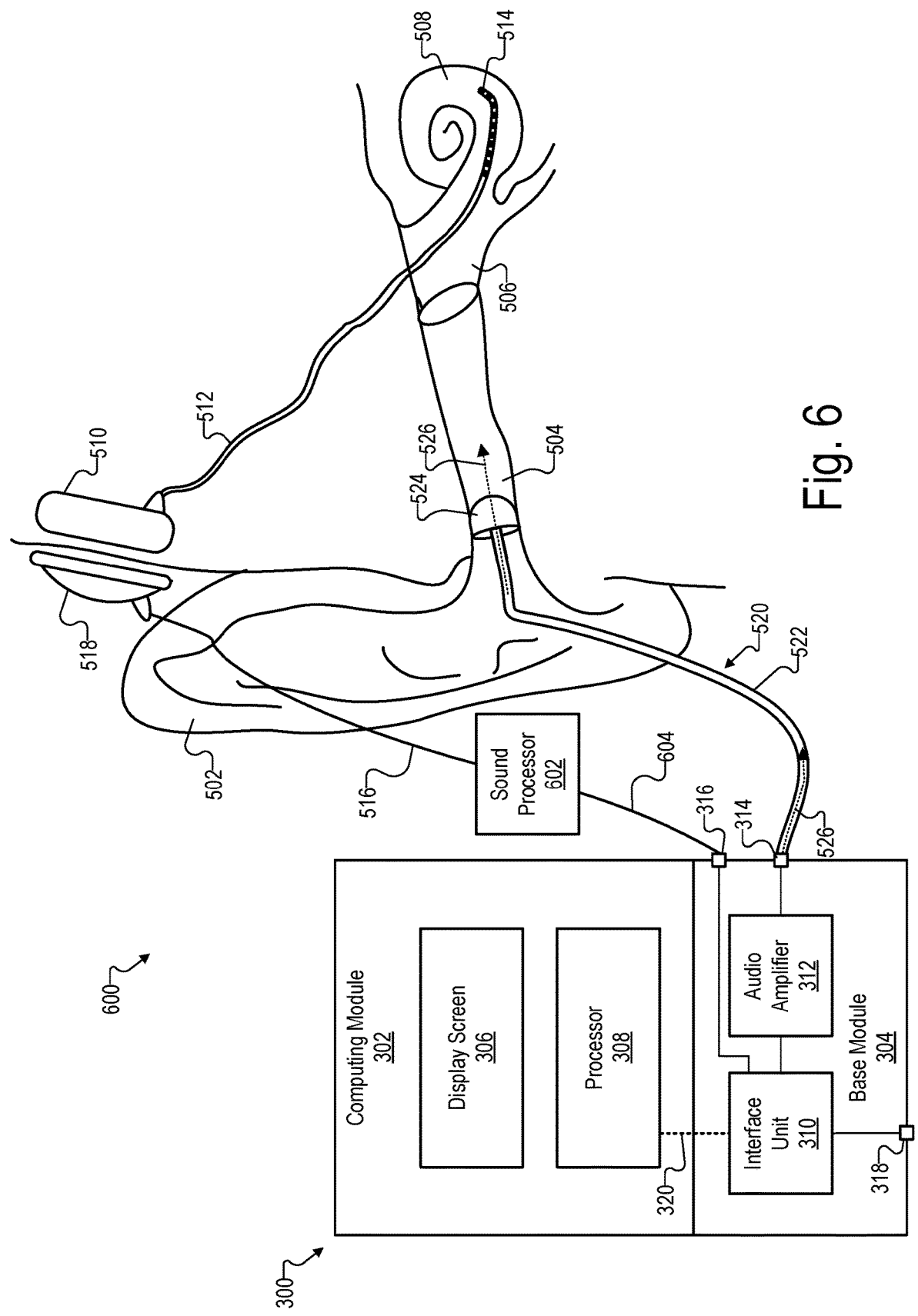

In configuration 500, headpiece 518 is connected directly to communications port 316 by way of cable 516. Hence, in configuration 500, interface unit 310 is configured to directly control cochlear implant 510. FIG. 6 illustrates an alternative configuration 600 in which a sound processor 602 is included in the communication path in between interface unit 310 and cochlear implant 510. Sound processor 602 may be similar to any of the sound processors (e.g., sound processor 104) described herein. In some examples, sound processor 602 is recipient-agnostic. In other words, sound processor 602 is not configured specifically for the recipient of cochlear implant 510. Rather, sound processor 602 may be used in a variety of different surgical procedures associated with a number of different recipients.

As shown, sound processor 602 is connected to communications port 316 by way of a cable 604. Sound processor 602 is also connected to headpiece 518 by way of cable 516. In this configuration, sound processor 602 may relay data and/or commands between interface unit 310 and cochlear implant 510.

As mentioned, during some surgical procedures, surgical drapes are placed over the ear and/or head of the recipient. The surgical drapes increase the spacing between headpiece 518 and of cochlear implant 510. In some scenarios, this may make it difficult to maintain proper alignment between headpiece 518 and a coil included in cochlear implant 510. This is because alignment between headpiece 518 and the coil of cochlear implant 510 is typically achieved using a magnet included within headpiece 518. With the increased spacing, a magnetic force of the magnet may not be sufficient to keep headpiece 518 properly aligned with the coil of cochlear implant 510.

Hence, in some examples, instead of using headpiece 518 to communicate with cochlear implant 510, a disposable coil may alternatively be connected to communications port 316. The disposable coil is not included in a housing, such as headpiece 518, that includes other components (e.g., a microphone and other electronics). As such, the disposable coil may have a relatively thin profile. This may allow the disposable coil to be inserted together with cochlear implant 510 into the same incision pocket within the recipient. In this manner, the disposable coil may be held in place by the incision pocket, thereby ensuring proper alignment of the disposable coil with the coil of cochlear implant 510.

Figure 7:
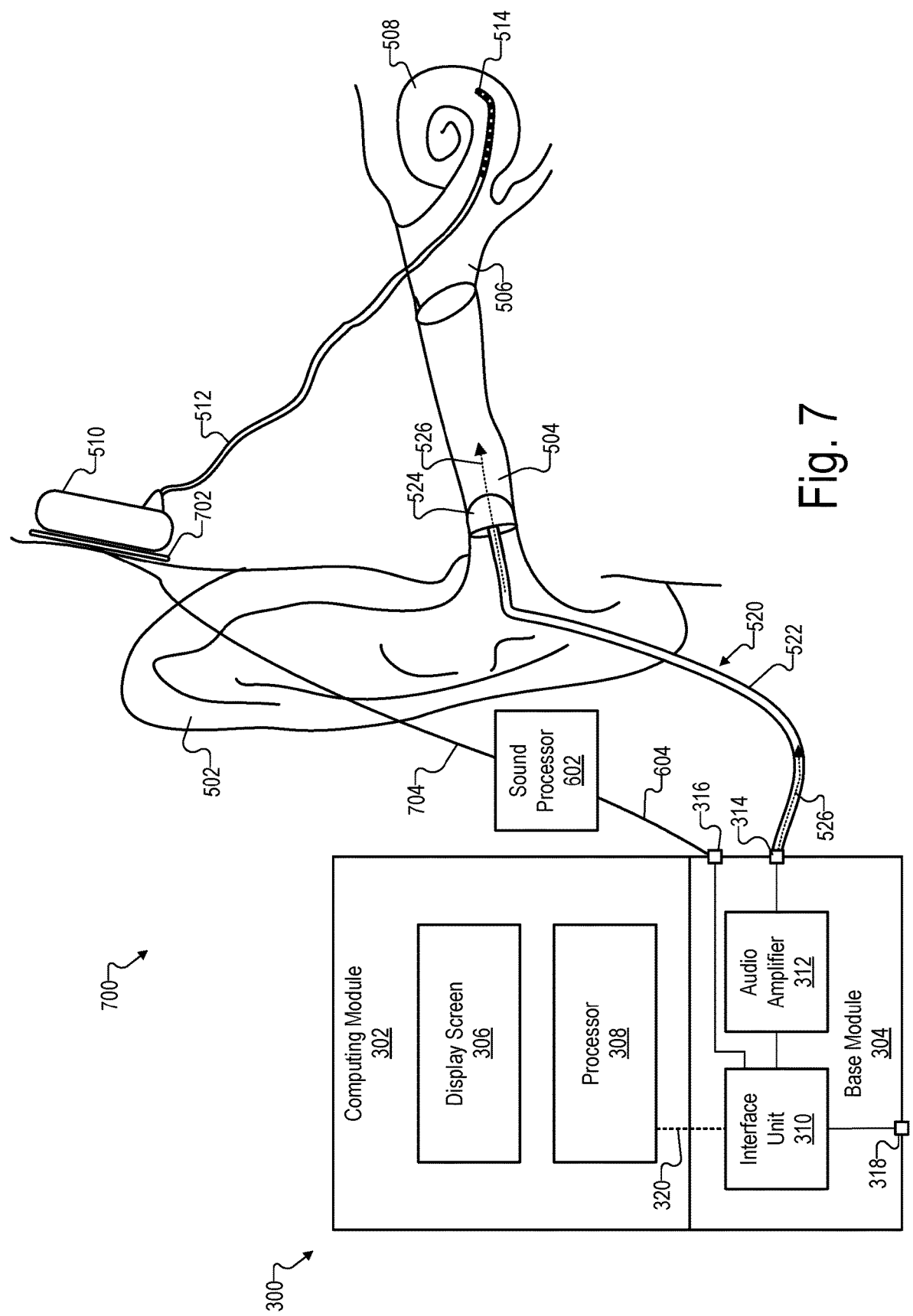

To illustrate, FIG. 7 shows an exemplary configuration 700 in which a disposable coil 702 and cochlear implant 510 are inserted into the same incision pocket of the recipient. As shown, headpiece 518 is not included in configuration 700. Rather, disposable coil 702 is connected to a cable 704, which connects to sound processor 602. Sound processor 602 is connected to communications port 316 by way of cable 706. In alternative embodiments, sound processor 602 may not be included in configuration 700. In these alternative embodiments, cable 704 may connect directly to communications port 316.

Figure 8:
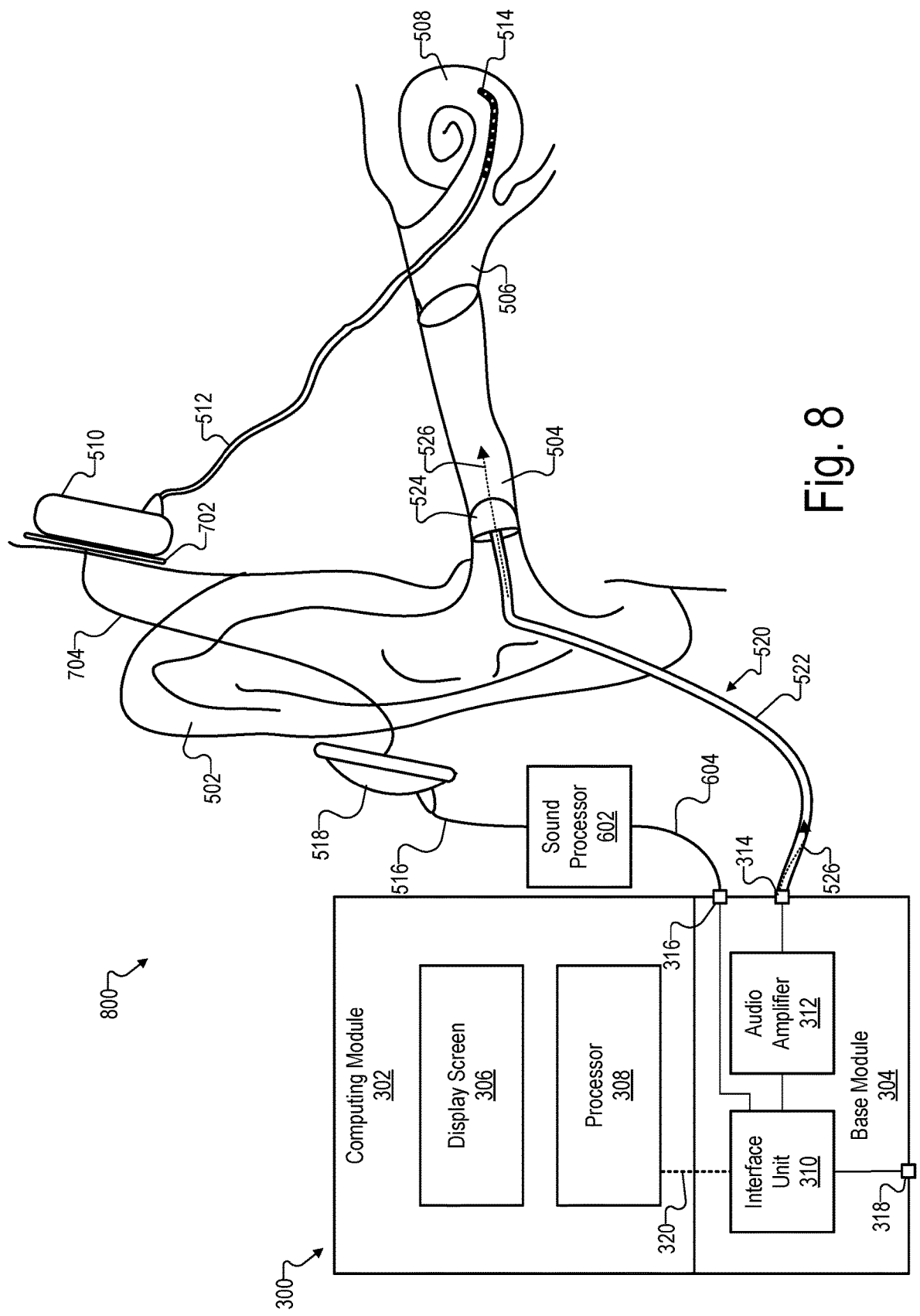

FIG. 8 shows an alternative configuration 800 that utilizes disposable coil 702. In configuration 800, disposable coil 702 is coupled directly to headpiece 518 by way of cable 704 (e.g., cable 704 may plug directly into a port of headpiece 518). As shown, headpiece 518 is connected to sound processor 602 by way of cable 516, and sound processor 602 is connected to communications port 316 by way of cable 604. In configuration 800, headpiece 518 does not need to be magnetically aligned with cochlear implant 510 because of the location of disposable coil 702 within the incision pocket.

In some examples, disposable coil 702 is included in a kit that is provided to a surgeon for a particular surgical procedure associated with its particular recipient. In these examples, disposable coil 702 is sterile or sterilizable. Upon completion of the surgical procedure, disposable coil 702 may be thrown away.

FIGS. 9A-9D illustrate various disposable coil configurations 900 that may be used in accordance with the systems and methods described herein. It will be recognized that disposable coil configurations 900 are merely examples of the many different types of disposable coil configurations that may be used in accordance with the systems and methods described herein.

Figure 9A:
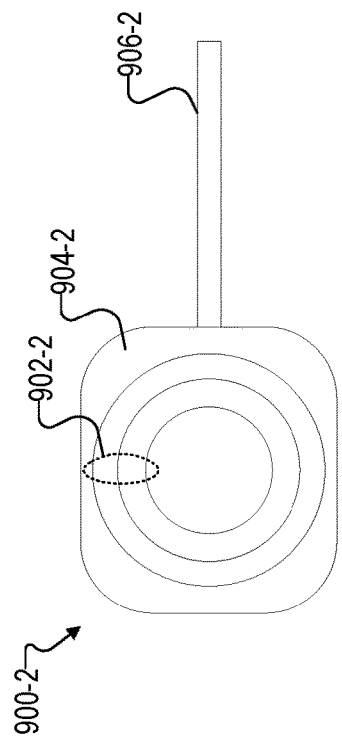
FIGS. 9A-9D illustrate various disposable coil configurations according to principles described herein.

As shown in FIG. 9A, disposable coil configuration 900-1 includes a coil 902-1 included within a casing 904-1. Casing 904-1 may be implemented by any suitable overmold or other thin-profile housing. The combination of coil 902-1 and casing 904-1 may implement disposable coil 702.

Disposable coil configuration 900-1 further includes a cable 906-1 connected to casing 904-1. Cable 906-1 may house one or more conductive vias (e.g., wires) conductively coupled to coil 902-1 and may implement cable 704.

In disposable coil configuration 900-1, a magnet 908 is included within casing 904-1. Magnet 908 may be configured to magnetically couple with a corresponding magnet included in a coil of cochlear implant 510. In this manner, coil 902 may stay aligned with the coil of cochlear implant 510 while coil 902-1 and casing 904-1 are located within the incision pocket.

Figure 9B:
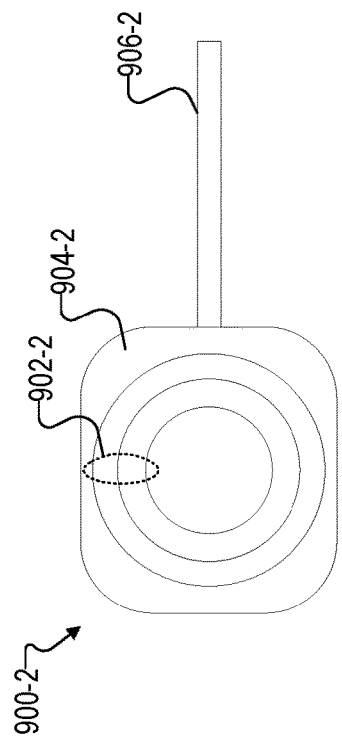

Disposable coil configuration 900-2 shown in FIG. 9B is similar to disposable coil configuration 900-1 in that disposable coil configuration 900-2 includes a coil 902-2, a casing 904-2, and a cable 906-2. However, unlike disposable coil configuration 900-2, disposable coil configuration 900-2 does not include magnet 908. Disposable coil configuration 900-2 may be used in situations where it may not be necessary to maintain alignment between coil 902-2 and the coil of cochlear implant 510 due to the snug fit of coil 902-2, casing 904-2, and cochlear implant 510 within the same incision pocket.

Figure 9C:
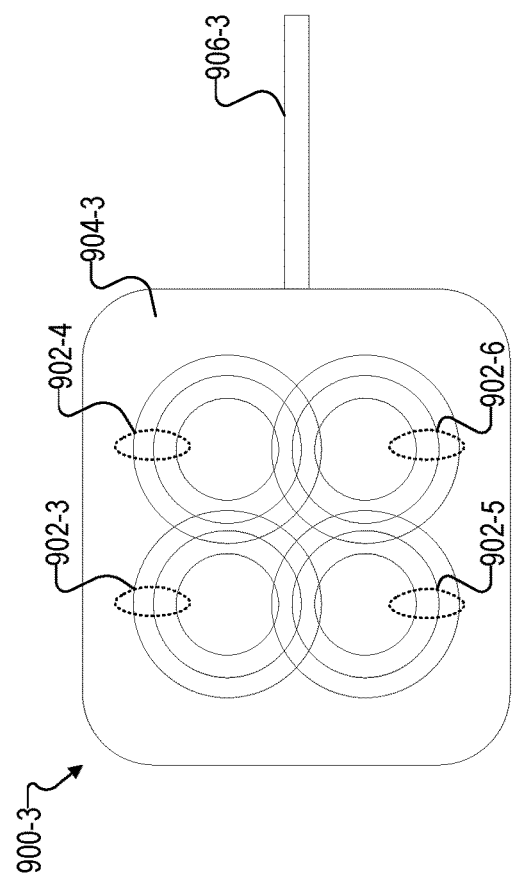

Disposable coil configuration 900-3 shown in FIG. 9C includes multiple coils (i.e., coils 902-3 through 902-6) included within a casing 904-3. Disposable coil configuration 900-3 further includes a cable 906-3 connected to casing 904-3. As shown, the surface area covered by the combination of coils 902-3 through 902-6 may be relatively large compared to that covered by a single coil (e.g., coil 902-1). This increased surface area coverage may further ensure that at least one of coils 902-3 through 902-6 is aligned with the coil of cochlear implant 510.

Figure 9D:
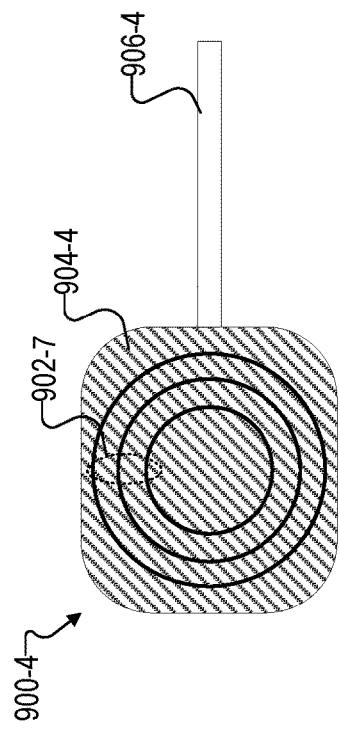

Disposable coil configuration 900-4 shown in FIG. 9D is similar to disposable coil configuration 900-2 in that disposable coil configuration 900-4 includes a coil 902-7, a casing 904-4, and a cable 906-4, while not including a magnet. However, as illustrated by the hatch lines of casing 904-4, one or more ferrite layers may be included within casing 904-4. The ferrite layers may be configured to assist in aligning coil 902-7 with the coil of cochlear implant 708.

Figure 10A:
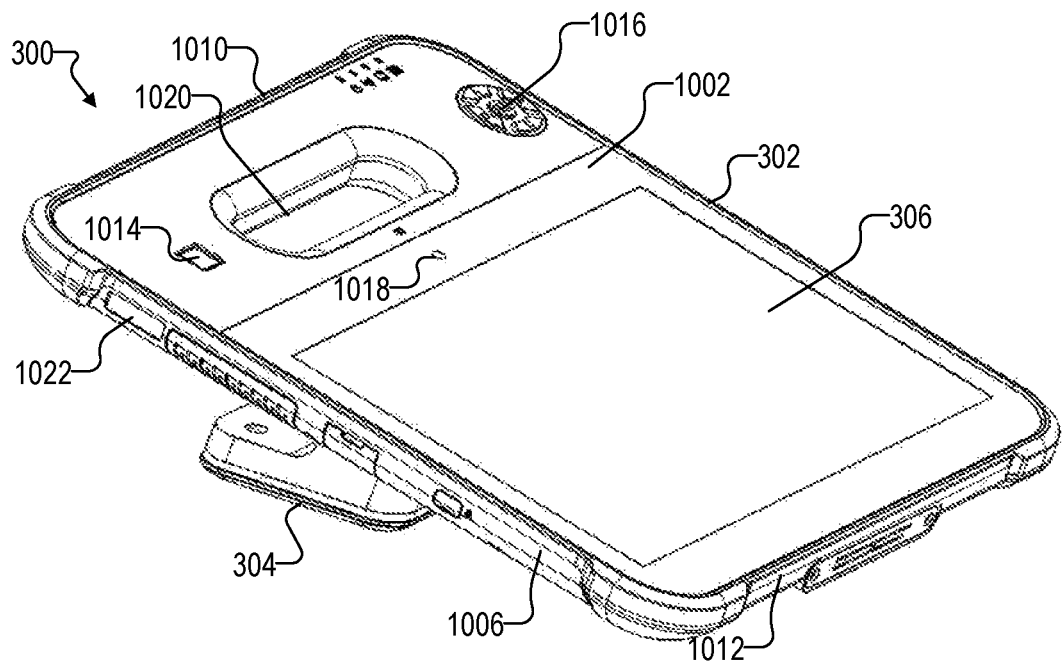
FIGS. 10A-13 illustrate an exemplary hardware implementation of the diagnostic system of FIG. 3 according to principles described herein.
Figure 10B:
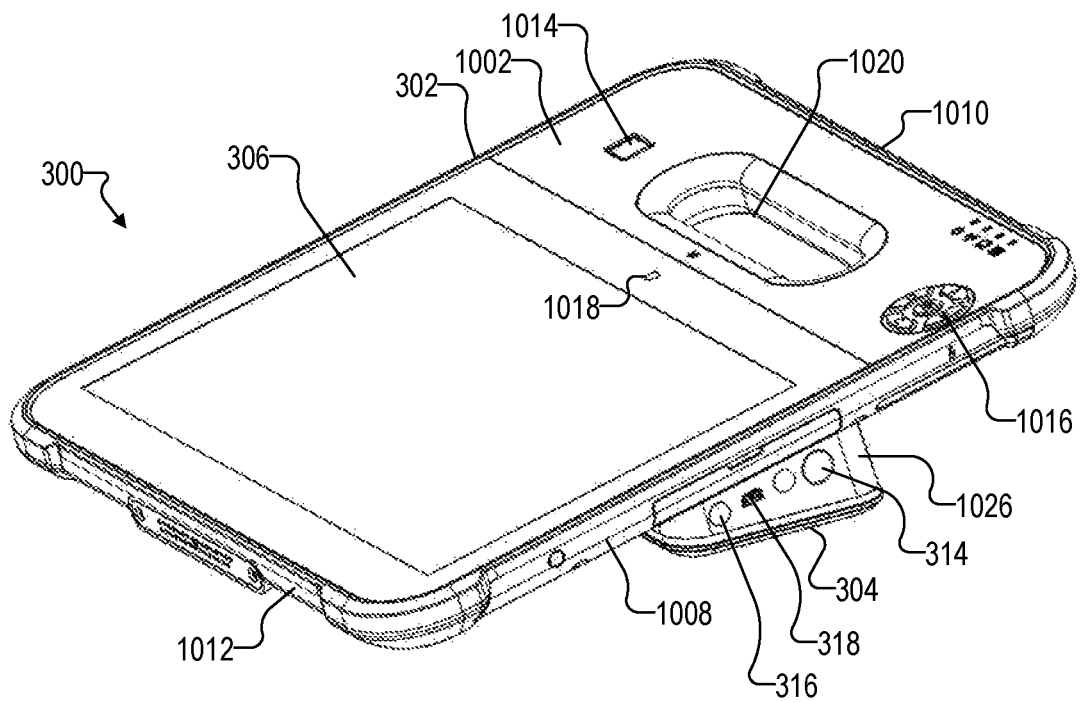
Figure 11A:
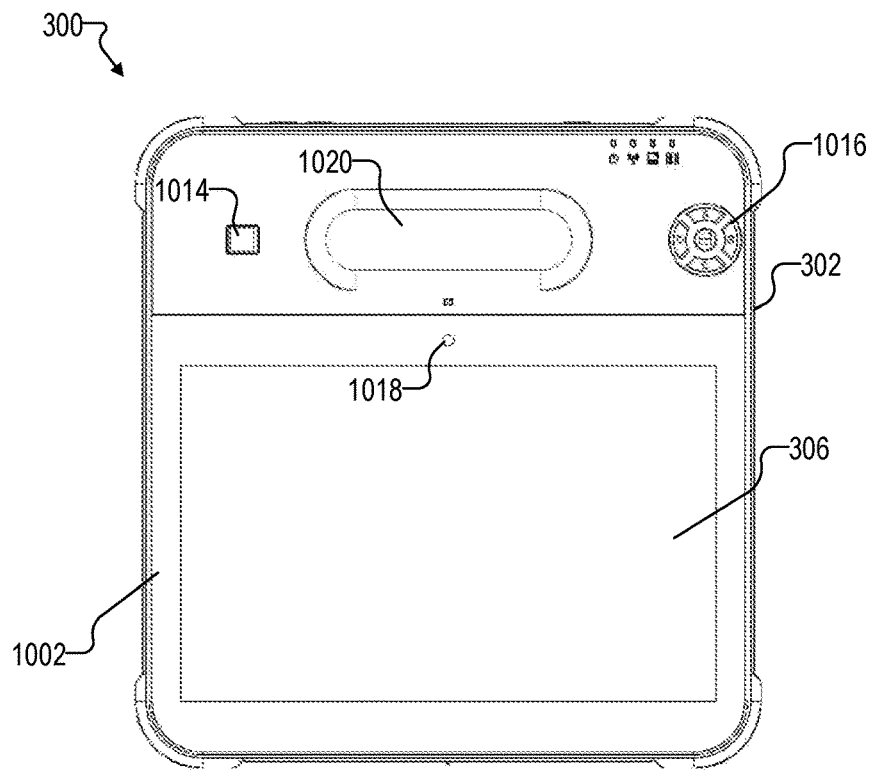
Figure 11B:
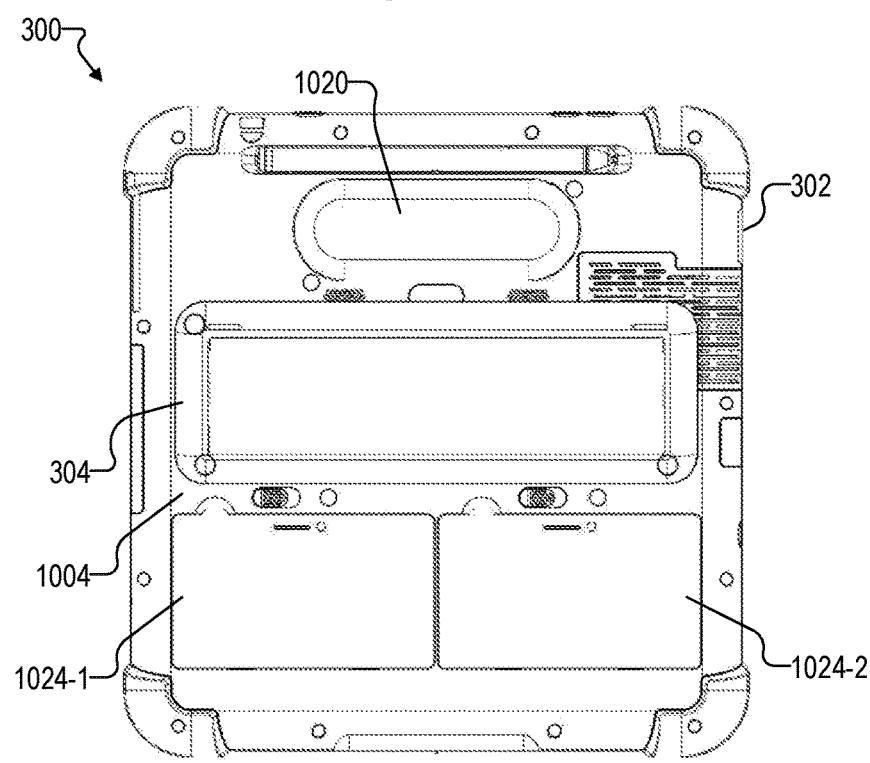
Figure 12A:
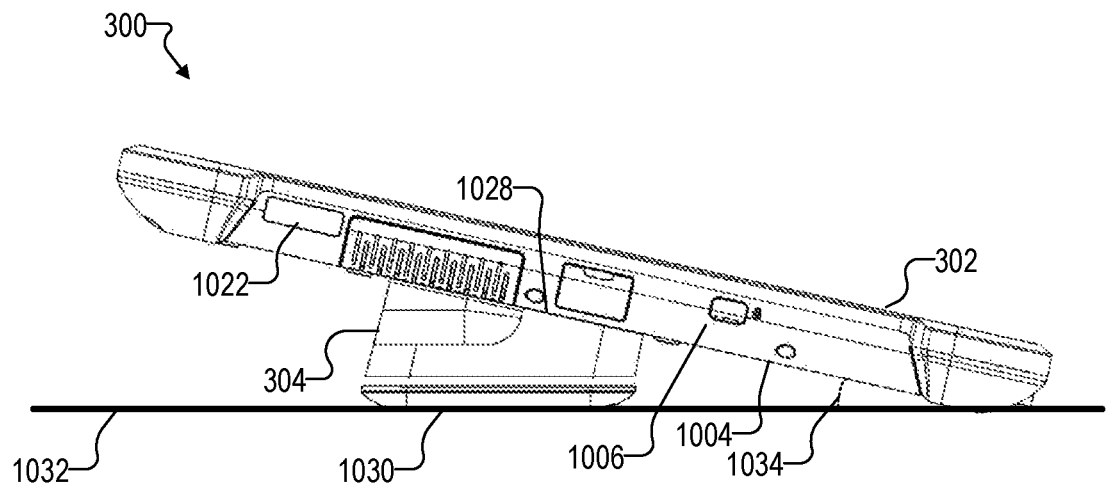
Figure 12B:
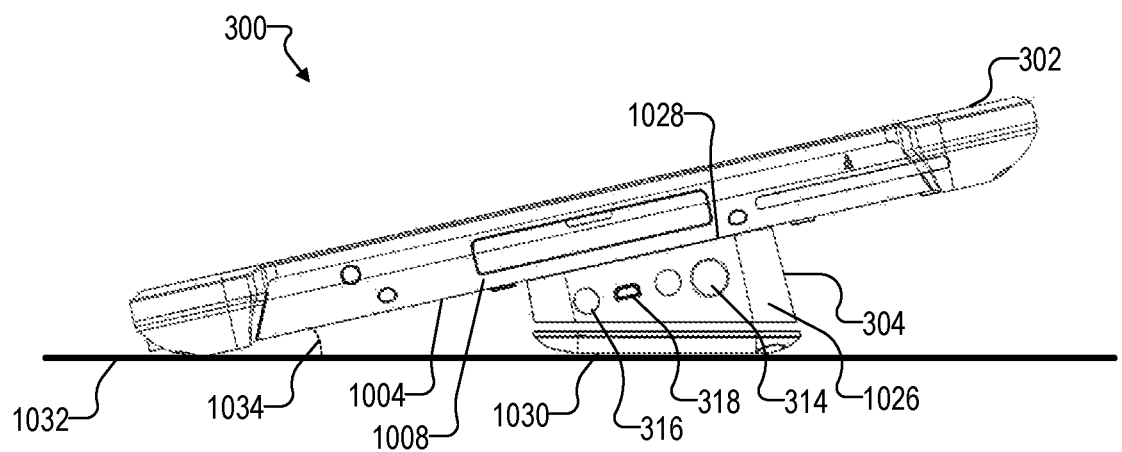
Figure 13:
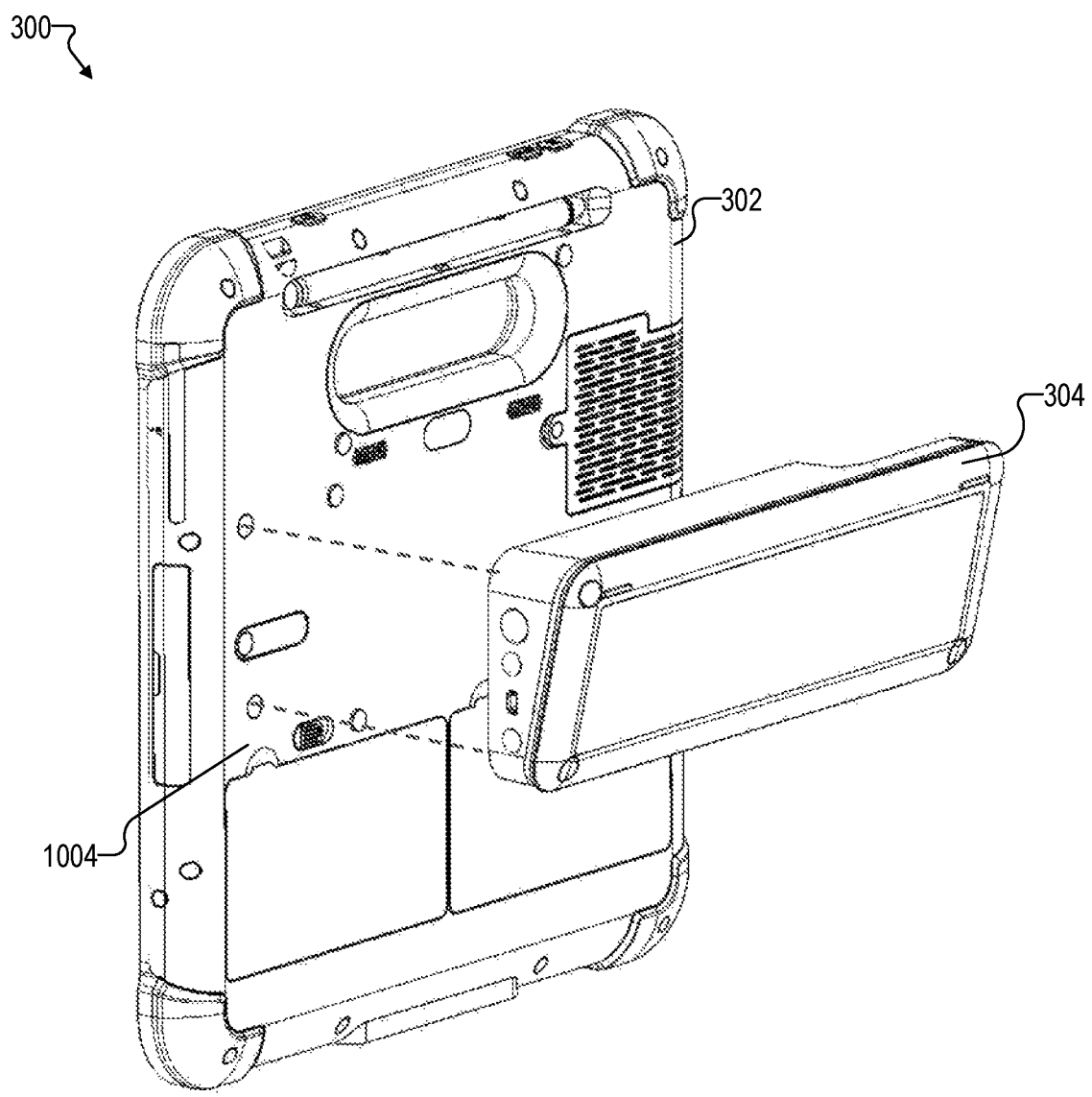

An exemplary hardware implementation of diagnostic system 300 will now be described in connection with FIGS. 10A-13. In particular, FIG. 10A shows a left perspective view of diagnostic system 300, FIG. 10B shows a right perspective view of diagnostic system 300, FIG. 11A shows a front view of diagnostic system 300, FIG. 11B shows a back view of diagnostic system 300, FIG. 12A shows a left side view of diagnostic system 300, FIG. 12B shows a right side view of diagnostic system 300, and FIG. 13 shows a rear perspective view of diagnostic system 300.

The hardware implementation of diagnostic system 300 illustrated in FIGS. 10A-13 includes computing module 302 and base module 304. As, illustrated computing module 302 includes a front side 1002, a back side 1004, a left side 1006, a right side 1008, a top side 1010, and a bottom side 1012.

Display screen 306 is located on front side 1002 of computing module 302. Various other components are also located on the front side 1002 of computing module 302. For example, a fingerprint scanner 1014, physical input buttons 1016, and a webcam 1018 all shown to be included on the front side 1002 of computing module 302. It will be recognized that any of these components may be located on any other side of computing module 302 as may serve a particular implementation.

Fingerprint scanner 1014 is configured to facilitate authentication of a user of diagnostic system 300. For example, fingerprint scanner 1014 may detect a fingerprint of the user and provide processor 308 with data representative of the fingerprint. Processor 308 may process the fingerprint data in any suitable manner (e.g., by comparing the fingerprint to known fingerprints included in a database) to authenticate the user.

Webcam 1018 may be configured to facilitate video communication by a user of diagnostic system 300 with a remotely located user (e.g., during a surgical procedure). Such video communication may be performed in any suitable manner.

Physical input buttons 1016 may be implemented, for example, by a directional pad and/or any other suitable type of physical input button. A user of diagnostic system 300 may interact with physical input buttons 1016 to perform various operations with respect to a diagnostic application being executed by processor 308. For example, the user may use the physical input buttons 1016 to interact with a graphical user interface displayed on display screen 306.

In some examples, physical input buttons 1016 may be configured to be selectively programmed (e.g., as hotkeys) to perform one or more functions associated with the diagnostic application. For example, a particular physical input button 1016 may be programmed by a user to start and/or stop acoustic stimulation being applied to a cochlear implant recipient by diagnostic system 300.

In some examples, processor 308 may be configured to wirelessly connect to an input device configured to be used by the user in connection with the diagnostic application. For example, processor 308 may be configured to wirelessly connect (e.g., via Bluetooth and/or any other suitable wireless communication protocol) to a keyboard, mouse, remote control, and/or any other wireless input device as may serve a particular implementation. In this manner, the user may selectively use physical input buttons 1016, a touchscreen capability of display screen 306, and/or a wireless input device to interact with diagnostic system 300.

Processor 308 may additionally or alternatively be configured to connect (e.g., via a wired or wireless connection) to a different computing device to facilitate communication with the different computing device. For example, processor 308 may wirelessly connect via a network to a remote computing device. In this configuration, processor 308 may receive data (e.g., recipient-specific data) from the remote computing device and/or transmit data to the remote computing device.

As shown, a hole 1020 may be formed within computing module 302 and configured to serve as a handle for diagnostic system 300. A user may grip computing module 302 by placing his or her fingers within hole 1020.

As shown, a barcode scanner 1022 may be located on left side 1006 of computing module 302. Barcode scanner 1022 may alternatively be located on any other side of computing module 302. In some examples, barcode scanner 1022 may be configured to scan for an activation code included on one or more components associated with the procedure being performed with respect to cochlear implant 510. The activation code may be used to associate (e.g., register) the components with cochlear implant 510.

As illustrated in FIG. 11B, computing module 302 may include batteries 1024-1 and 1024-2. Batteries 1024 may be configured to provide operating power for various components included within computing module 302 and base module 304. In some examples, batteries 1024 may be hot-swappable. In other words, one of batteries 1024 (e.g., battery 1024-1) may be removed and replaced while the other battery (e.g., battery 1024-2) is used to provide power to computing module 302 and base module 304.

As illustrated in FIGS. 10B and 12B, ports 314, 316, and 318 are located on a side surface 1026 of base module 304. Ports 314, 316, and 318 may alternatively be located on any other surface of base module 304.

As described above, base module 304 may be configured to serve as a stand for computing module 302 while base module 304 is attached to computing module 302. The stand functionality of base module 304 is illustrated in FIGS. 12A-12B.

As shown, base module 304 includes a top surface 1028 configured to selectively attach to back side 1004 of computing module 302. Base module 404 may alternatively attach to any other side of computing module 302. Base module 304 further includes a bottom surface 1030 configured to be placed on a resting surface 1032. Bottom surface 1030 is angled with respect to back side 1004 of computing module 302. This provides a viewing angle 1034 for display screen 306 that is greater than zero degrees with respect to resting surface 1032. In some examples, base module 304 may be adjustable to selectively provide different viewing angles for display screen 306 with respect to resting surface 1032. This adjustability may be realized in any suitable manner. For example, a user may manually adjust bottom surface 1030 to different angles with respect to back side 1004 of computing module 302.

FIG. 13 illustrates an exemplary configuration in which base module 304 is detached from computing module 302. Base module 304 may be detached from computing module 302 in any suitable manner. For example, base module 304 may include one or more locking mechanisms that may be actuated by a user to detach base module 304 from computing module 302.

Figure 14:
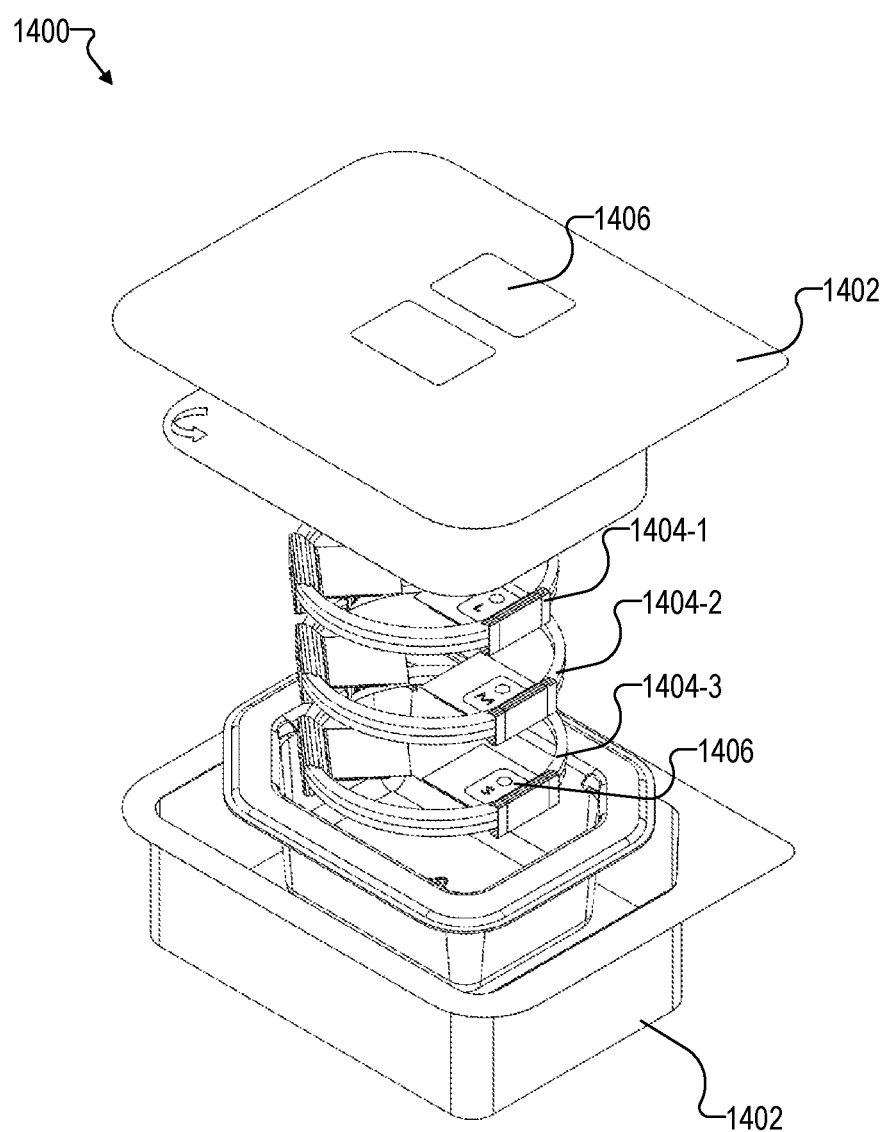
FIG. 14 illustrates a disassembled sterile kit according to principles described herein.

FIG. 14 illustrates a disassembled sterile kit 1400 that may be provided for use in conjunction with diagnostic system 300 during a procedure associated with a cochlear implant. Sterile kit 1400 includes packaging 1402 and a plurality of sound delivery apparatuses 1404 (e.g., sound delivery apparatus 1404-1 through sound delivery apparatus 1404-3). One or more other components may be included in sterile kit 1400 as may serve a particular implementation. For example, sterile kit 1400 may further include one or more disposable coils, such as any of the disposable coils described herein.

As shown, packaging 1402 may include an activation code label 1406. Activation code label 1406 may be scanned by barcode reader 1022 to associate the contents of sterile kit 1400 with a particular cochlear implant and/or recipient.

Sound delivery apparatuses 1404 may each be of a different size. For example, sound delivery apparatus 1404-1 may be a "large", sound delivery apparatus 1404-2 may be a "medium", and sound delivery apparatus 1404-3 may be a "small". Each sound delivery apparatus 1404 may include a label (e.g., label 1406) that may be color coded, include a printed activation code, or otherwise labeled as may serve a particular implementation.

In this manner, a surgeon or other user may select an appropriately sized sound delivery apparatus 1404 for use with a particular recipient. Each sound delivery apparatus 1404 may be sterile so that they may be used in an operating room.

Figure 15:
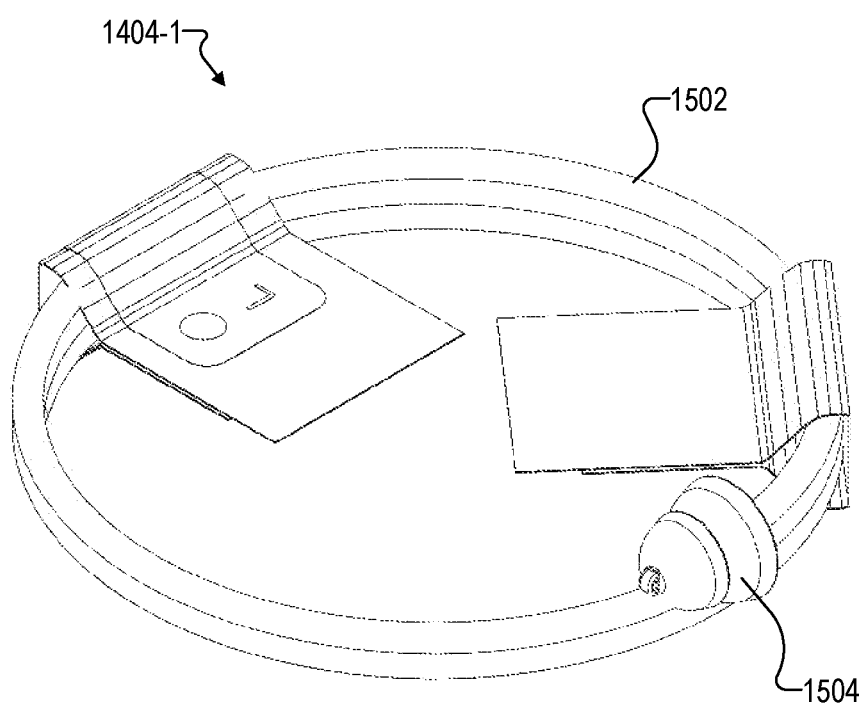
FIG. 15 shows an exemplary sound delivery apparatus according to principles described herein.

FIG. 15 shows sound delivery apparatus 1404-1 in more detail. As shown, sound delivery apparatus 1404-1 includes tubing 1502 and an ear insert 1504 connected to a distal end of tubing 1502. Sound delivery apparatus 1404-1 may further include a luer and/or any other component as may serve a particular implementation. Ear insert 1504 is configured to be placed at or within an entrance to an ear canal of a recipient of a cochlear implant. A proximal end of tubing 1502 may be connected to audio output port 314. In this configuration, acoustic stimulation may be delivered to a recipient of a cochlear implant by way of tubing 1502.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A diagnostic system for use during a procedure associated with a cochlear implant, the diagnostic system comprising:
   a sound delivery apparatus comprising tubing that has a distal portion configured to be placed in or near an entrance to an ear canal of a recipient of the cochlear implant;
   a computing module comprising:
      a display screen, and
      a processor configured to execute a diagnostic application and direct the display screen to display a graphical user interface associated with the diagnostic application; and
   a base module configured to attach to the computing module and serve as a stand for the computing module, the base module housing an interface unit configured to be communicatively coupled to the processor and to the cochlear implant while the base module is attached to the computing module, the base module comprising an audio output port configured to be selectively coupled to the sound delivery apparatus;
   wherein the interface unit is further configured to generate acoustic stimulation and deliver the acoustic stimulation to the recipient of the cochlear implant by way of the audio output port and the sound delivery apparatus.

2. The diagnostic system of claim 1, wherein the base module further comprises:
   a communications port configured to be selectively coupled to a coil configured to wirelessly communicate with the cochlear implant.

3. The diagnostic system of claim 2, wherein the interface unit is further configured to:
   receive recording data associated with the acoustic stimulation from the cochlear implant by way of the coil and the communications port.

4. The diagnostic system of claim 3, wherein the recording data is representative of an evoked response that occurs within the recipient in response to the acoustic stimulation.

5. The diagnostic system of claim 3, wherein the interface unit is configured to transmit the recording data to the processor.

6. The diagnostic system of claim 5, wherein the processor is configured to process the recording data in accordance with the diagnostic application.

7. The diagnostic system of claim 3, wherein the interface unit is configured to transmit a command to the cochlear implant by way of the communications port and the coil, the command configured to direct the cochlear implant to acquire the recording data using one or more electrodes disposed on an electrode array that is coupled to the cochlear implant.

8. The diagnostic system of claim 1, wherein the base module further houses an audio amplifier configured to amplify the acoustic stimulation before the acoustic stimulation is delivered to the recipient.

9. The diagnostic system of claim 1, wherein the interface unit is configured to receive a command from the processor to generate the acoustic stimulation and generate the acoustic stimulation in response to the command.

10. The diagnostic system of claim 1, wherein the base module is configured to detach from the computing module and communicatively couple to a computing device other than the computing module.

11. The diagnostic system of claim 10, wherein the base module comprises a port configured to attach to a cable that communicatively couples the interface unit to the computing device while the base module is detached from the computing module.

12. The diagnostic system of claim 1, wherein a bottom surface of the base module is angled with respect to the computing module such that when the base module is placed on a resting surface and used as the stand for the computing module, the base module provides a viewing angle for the display screen that is greater than zero degrees with respect to the resting surface.

13. The diagnostic system of claim 12, wherein the base module is adjustable to selectively provide different viewing angles from the display screen with respect to the resting surface.

14. The diagnostic system of claim 1, wherein the computing module further comprises a fingerprint scanner configured to facilitate authentication of a user of the diagnostic system.

15. The diagnostic system of claim 1, wherein the computing module further comprises a barcode scanner configured to scan for an activation code included on one or more components associated with the procedure.

16. The diagnostic system of claim 1, wherein the computing module further comprises one or more physical input buttons configured to be selectively programmed to perform one or more functions associated with the diagnostic application.

17. The diagnostic system of claim 1, wherein the processor is configured to wirelessly connect to an input device configured to be used by a user in connection with the diagnostic application.

18. The diagnostic system of claim 1, further comprising a disposable coil configured to connect to the interface unit.

* * * * *